(12) United States Patent
Kwon et al.

(10) Patent No.: US 7,799,811 B2
(45) Date of Patent: Sep. 21, 2010

(54) AGENT FOR PREVENTION AND TREATMENT OF CANCER COMPRISING OXADIAZOLE UREA COMPOUND OBSTRUCTING ACTIVITY OF STAT

(75) Inventors: Byoung-Mog Kwon, Daejon (KR); Dong Cho Han, Daejon (KR); Kwang-Hee Son, Daejon (KR); Dae-Seop Shin, Chungcheongbuk-do (KR); Jimin Lee, Gyeongsangbuk-do (KR)

(73) Assignee: Korea Research Institute of Bioscience and Biotechnology, Taejeon-Si (KR)

( * ) Notice: Subject to any disclaimer, the term of this patent is extended or adjusted under 35 U.S.C. 154(b) by 0 days.

(21) Appl. No.: 11/839,298

(22) Filed: Aug. 15, 2007

(65) Prior Publication Data

US 2008/0051442 A1 Feb. 28, 2008

(30) Foreign Application Priority Data

Aug. 22, 2006 (KR) ...................... 10-2006-0079561

(51) Int. Cl.
*A61K 31/4245* (2006.01)
*A61P 35/00* (2006.01)

(52) U.S. Cl. ..................................... 514/364
(58) Field of Classification Search ........................ None
See application file for complete search history.

(56) References Cited

OTHER PUBLICATIONS

Ji et al. Occupational Exposure to Pesticides and Pancreatic Cancer. American Journal of Industrial Medicine, 38, 92-99, 2001.*
Dich et al. Prostate cancer in pesticide applicators in Swedish agriculture, The Prostate: 34: 100-112, 1998.*
Davis et al. Family pesticide use and childhood brain cancer. Archives of Environmental Contamination and Toxicology, 24, 87-92, 1993.*
Barthel. Increased mortality from esophageal cancer, stomach cancer and skin melanoma in pesticide-exposed pest control operators in the DDR. Arch Geschwulstforsch, 55(6): 481-8, 1985.*
Lee et al. Pesticide use and colorectal cancer risk in the Agricultural Heatlh Study, Int. J. Cancer, 121, 339-346, 2007.*
Hunter et al. Pesticide residues and breast cancer: the harvest of a silent spring?. Journal of the National Cancer Institute, vol. 85, No. 8, Apr. 21, 1993.*
Johnson et al. Relationships between drug activity in NCI preclinical in vitro and in vivo models and early clinical trials. British Journal of Cancer, 2001, 64(10): 1424-1431.*
Sausville et al. Contributions of human tumor xenografts to anticancer drug development. Cancer Res 2006, 66:(7), Apr. 1, 2006.*
Freshney. Culture of Animal Cells. A manual of basic technique. Alan R. Liss, 1983, New York, p. 4.*
Dermer (Bio/Technology, 1994, 12:320).*
Gura (Science, v278, 1997, pp. 1041-1042).*
James E. Darnell, Jr., Phosphotyrosine Signaling and the Single . . . , Proc. Natl. Acad. Sci., vol. 94, pp. 11767-11769, 1997.
Hua Yu., et al., The Stats of Cancer-New . . . , Nature Reviews Cancer, vol. 4, pp. 97-105, 2004.
Catlett-Falcone, R., et al., Constitutive Activation of STAT3 Signaling . . . , Immunity, vol. 10, pp. 105-115, 1999.
Guilian Niu, et al., Constitutive STAT3 Activity Up-Regulates . . . , Oncogene, vol. 21, pp. 2000-2008, 2002.
Tianhong Wang, et al., Regulation of the Innate and Adaptive Immune . . . , Nature Medicie, vol. 10, pp. 48-54, 2004.
Mora, L.B., et al, "Constitutive Activation of Stat3 in Human Prostate Tumors and Cell Lines: Direct Inhibition of Stat3 Signaling Induces Apoptosis of Prostate Cancer Cells", Cancer Res., Nov. 15, 2002, vol. 62, pp. 6659-6666.
Aggarwal, B.B., et al., "Targeting Signal-Transducer-and-Activator-of Transcription-3 for Prevention and Therapy of Cancer. Modem Target but Ancient Solution." Ann. N.Y. Acad. Sci., vol. 1091, pp. 151-169 (2006).
Shin, D.-S., et al, "Cryptotanshinone Inhibits Constitutive Signal Transducer and Activator of Transcription 3 Function through Blocking the Dimerization in DU145 Prostate Cancer Cells", Cancer Res., Jan. 1, 2009, vol. 69, pp. 193-202.

\* cited by examiner

*Primary Examiner*—Brandon J Fetterolf
*Assistant Examiner*—Anna Pagonakis
(74) *Attorney, Agent, or Firm*—Lucas & Mercanti, LLP

(57) ABSTRACT

Disclosed herein is an agent for preventing and treating cancer which includes an oxadiazole urea compound represented by Chemical Formula 1, below, as an effective ingredient. The oxadiazole urea compound effectively inhibits the growth of cancer cell lines and the activity of STAT3, and may be used in the prevention and treatment of cancer.

[Chemical Formula 1]

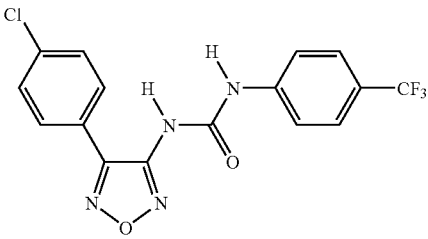

2 Claims, No Drawings

AGENT FOR PREVENTION AND TREATMENT OF CANCER COMPRISING OXADIAZOLE UREA COMPOUND OBSTRUCTING ACTIVITY OF STAT

CROSS-REFERENCE TO RELATED APPLICATION

This application claims the benefit of Korean Patent Application No. 10-2006-079561, filed Aug. 22, 2006 with the Korean Intellectual Property Office, the disclosure of which is incorporated herein in its entirety by reference.

BACKGROUND OF THE INVENTION

1. Field of the Invention

The present invention relates to an agent for preventing and treating cancer comprising an oxadiazole urea compound as an effective ingredient, the agent effectively inhibiting the growth of a cancer cell line and STAT3 activity.

2. Description of the Related Art

Although the incidence of cancer is increasing with the advance of civilization, the treatment of cancer patients depends on surgery, radiotherapy, and chemotherapy, involving the administration of about forty anticancer substances having high cytotoxicity. Since these therapies are mostly limited to early cancer patients or specific cancer types, cancer death rates are increasing.

Cancer is the most incurable disease, and mechanisms of cancer incidence and progress are similar to those of vascular diseases, rheumatoid arthritis and other immunological diseases. In this regard, many studies involving anticancer agents have been performed. Selective anticancer agents, which act on specific molecular targets, are gaining more attention because they provide safer and more effective strategies and are applicable in personalized medicine and combination therapy.

Signal transducers and activators of transcription (STAT) proteins (STAT1, STAT2, STAT3, STAT4, STAT5 and STAT6), which have a molecular weight ranging from 84 to 113 kDa, contain an SH2 domain, which recognizes one or more phosphotyrosines present in the cytoplasmic domains of some activated receptors.

The SH2 (Src Homology-2) domain serves as a phosphorylation-dependent switch to control receptor recognition and DNA binding. Thus, STAT proteins enable the direct linkage of the activity of cell surface receptors to gene regulation (James R. Darnell, Jr., Proceedings of the National Academy of Sciences. USA, 94, 11767-11769, (1997)).

In animal cells, activation of the latent cytoplasmic STAT molecules is accomplished either through cell surface receptors for cytokines and their non-covalently-associated Jak kinases or by growth factor receptors having intrinsic tyrosine kinase activity.

Binding of the cognate ligand to the cell surface receptor causes the phosphorylation of tyrosines in the cytoplasmic regions of the receptor, thereby creating docking sites for the STAT SH2 domain. The consequent recruitment of the STATs to the receptor leads, in turn, to their phosphorylation on tyrosine by the Jak or receptor kinases. The phosphorylated STATs form SH2-mediated dimers and are then translocated to the nucleus, where they bind to DNA and direct specific transcriptional initiation.

STAT signaling is assumed to be terminated by dephosphorylation and proteolytic degradation.

Constitutive activation of STAT proteins, in particular, STAT1, STAT3 and STAT5, is found in a wide variety of human cancers. In particular, STAT3 is activated in blood malignancies, such as leukemias, as well as solid tumors, such as breast cancer, head and neck cancer, melanoma, ovarian carcinoma, lung cancer, pancreatic carcinoma and prostate carcinoma. Thus, STAT3 is an important anticancer target (Hua Yu and Richard Jove, Nature Reviews Cancer (2004), 4, 97-105).

Blocking STAT3 function is important as a basic technique for developing more effective and substantial anticancer drugs by controlling tumors through multiple anticancer mechanisms involving apoptosis, angiogenesis inhibition and blocking of immune escape, and is expected to have high therapeutic effects compared to conventional anticancer drugs acting through a single mechanism Also, since STAT proteins participate in functions of various types of cells as well as in tumors, the development of STAT3 inhibitors may be utilized as a major basic technique having ripple effects on the development of immune suppressors and antidiabetic drugs.

SUMMARY OF THE INVENTION

Thus, the present inventors found that an oxadiazole urea compound regulates the expression and activity of STATs. The compound was found to inhibit the growth of various human cancer cell lines, and to thus have potential as a preventive and therapeutic agent for cancer, leading to the present invention.

It is therefore an object of the present invention to provide an agent for preventing and treating cancer comprising an oxadiazole urea compound or a pharmaceutically acceptable salt thereof as an effective ingredient.

In order to accomplish the above object, the present invention provides an agent for preventing and treating cancer comprising an oxadiazole urea compound or a pharmaceutically acceptable salt thereof as an effective ingredient.

DESCRIPTION OF THE PREFERRED EMBODIMENTS

In one aspect, the present invention provides an agent for preventing and treating cancer comprising the oxadiazole urea compound represented by Chemical Formula 1, below, or a pharmaceutically acceptable salt thereof, as an effective ingredient.

[Chemical Formula 1]

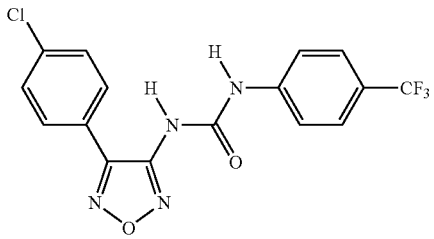

The oxadiazole urea compound has the molecular formula of $C_{16}H_{10}ClF_3N_4O_2$, and has physicochemical properties as follows. The compound is a white solid powder, which is well dissolved in a polar solvent, such as DMSO, is not dissolved in a nonpolar solvent, such as hexane, and has a melting point of 214□ and a molecular weight of 382.72.

The oxadiazole urea compound may be synthesized through a synthesis process comprising three steps, as shown in Reaction Formula 1, below. The synthesis process is schematically shown below.

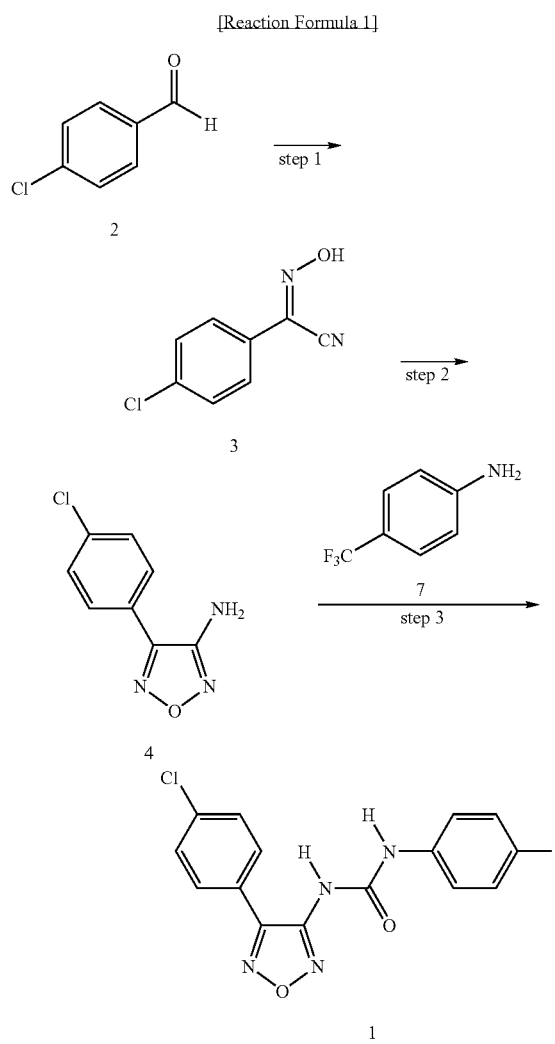

First, ρ-chlorobenzaldehyde (2) as a starting material at step 1 is reacted with amino-hydroxide (NH₂OH) and N-chlorosuccinimide (NCS), and the reaction product is reacted with potassium cyanide to yield a cyano compound (3) (Step 1). The cyano compound (3) produced at step 1 is reacted with amino-hydroxide, and the reaction product is treated with a base solution to yield an oxadiazole compound (4) (Step 2). Then, the oxadiazole compound (4) produced at step 2 is reacted with 4-trifluoromethyl aniline and triphosgene to yield the oxadiazole urea compound (1) (Step 3).

Hereinafter, the present method will be described in more detail at each step.

At step 1, as shown in Reaction Formula 2, below, the starting material ρ-chlorobenzaldehyde (2) is dissolved in methanol solvent, mixed with amino-hydroxide and sodium bicarbonate, and allowed to react while being stirred for two hours. After the reaction is completed, the reaction product is dissolved in dimethylformamide (DMF) and allowed to react with N-chlorosuccinimide (NCS) to yield an oxime compound (5). The oxime compound (5) is dissolved in ethylether solvent and allowed to react with potassium cyanide to yield a cyano compound (3).

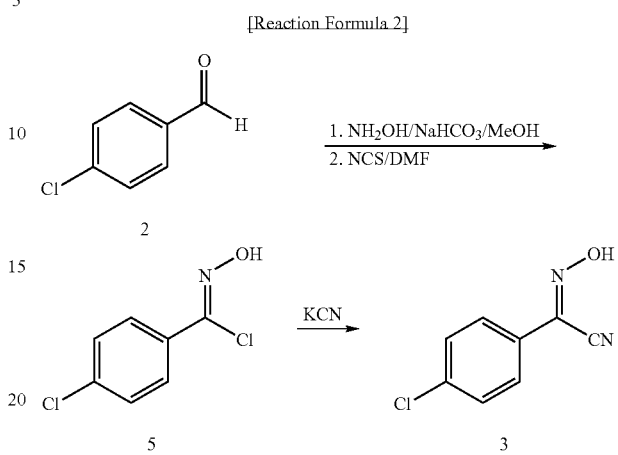

At step 2, as shown in Reaction Formula 3, below, the cyano compound (3) produced at step 1 is dissolved in methanol solvent, mixed with amino-hydroxide and sodium bicarbonate, and allowed to react for 12 hours. After the reaction is completed, the reaction product (6) is dissolved in an aqueous solution of 2N sodium hydroxide, refluxed for 12 hours, and then cooled and filtered to yield a compound (4) having an oxadiazole ring.

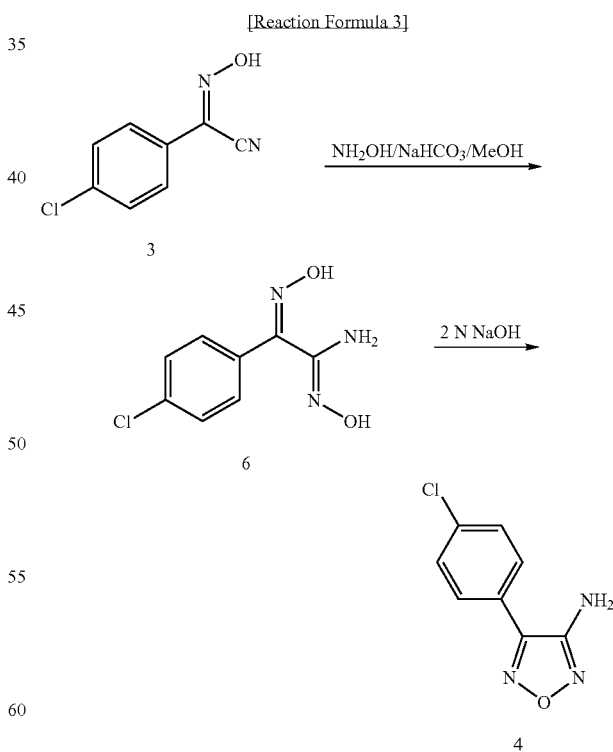

At step 3, the oxadiazole compound (4) produced at step 2 is dissolved in THF solvent, mixed with a solution of 4-trifluoromethyl aniline and triphosgene, which are dissolved in the same solvent, and allowed to react for two hours. After the reaction is completed, the reaction mixture is filtered, dried, and recrystallized in methanol to obtain the pure oxadiazole urea compound (1) of the present invention.

The present invention provides the use of the oxadiazole urea compound represented by Chemical Formula 1 or a pharmaceutically acceptable salt thereof.

In detail, the agent for preventing and treating cancer comprising the oxadiazole urea compound represented by Chemical Formula 1 or a pharmaceutically acceptable salt thereof as an effective ingredient may be present in the form of a pharmaceutical composition. The pharmaceutical composition according to the present invention inhibits signal transducers and activators of transcription (STAT) proteins, which are found in activated forms in a wide variety of cancers. Thus, the present composition may be used as a novel preventive and therapeutic agent for cancer through multiple anticancer mechanisms involving apoptosis (Catlett-Falcone R. et al., Immunity (1999), 10, 105-115), angiogenesis inhibition (Niu, G. et al., Oncogene (2002), 21, 2000-2008), and blocking of immune escape (Wang T. et al., Nature Medicine (2004), 10, 48-54). The inhibitory activity of the present compound toward STAT3 will be described in detail, below.

A dual luciferase assay for evaluating the inhibitory activity of the present compound against STAT3 revealed that the present compound of Chemical Formula 1 inhibited 50% of STAT3 activity at 2.5 to 3.0 µM in human colorectal carcinoma HCT116 cells transfected with firefly luciferase, whose expression increases with STAT3 activity.

Another test was conducted to determine whether the present compound of Chemical Formula 1 has an effect of inhibiting the growth of other human carcinoma cell lines, including breast cancer MDA-MB-231 cells, colorectal carcinoma HCT116 cells, and colon carcinoma SW620 cells. This test resulted in the present compound having a growth inhibitory effect of 50% against the cancer cell lines at a dose from 15 to 80 µM.

As described above, the pharmaceutical composition comprising the compound of Chemical Formula 1 or a pharmaceutically acceptable salt thereof as an effective ingredient may be useful in the prevention and treatment of various types of cancer, including colorectal cancer, stomach cancer, prostate cancer, breast cancer, kidney cancer, liver cancer, brain tumors, lung cancer, uterine cancer, colon cancer, bladder cancer and pancreatic cancer, through multiple anticancer mechanisms involving inhibiting the growth of various cancer cell lines, thus effectively inhibiting the activity of STAT proteins in the cancer cell lines.

When intended for use as a medicament, the pharmaceutical composition comprising the oxadiazole urea compound represented by Chemical Formula 1 or a pharmaceutically acceptable salt thereof as an effective ingredient may be formulated into various dosage forms for oral or parenteral administration upon clinical application, but is not limited thereto.

When formulated, in addition to the compound of Chemical Formula 1, the pharmaceutical composition may include pharmaceutically or physiologically acceptable diluents, excipients or carriers, which are exemplified by fillers, thickeners, binders, humectants, disintegrators and surfactants. The present composition may be administered orally, or via various routes, for example, intravenously, intraperitoneally, subcutaneously, intrarectally and topically.

Examples of carriers, excipients and diluents suitable for the pharmaceutical composition of the present invention include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methyl hydroxybenzoate, propyl hydroxybenzoate, talc, magnesium stearate and mineral oils. The composition may further include fillers, anti-coagulating agents, lubricants, humectants, perfumes, emulsifiers and antiseptics.

Examples of solid formulations for oral administration include tablets, pills, powders, granules and capsules. The solid formulations may prepared by mixing the composition with at least one excipient selected from among starch, calcium carbonate, sucrose, lactose, gelatin, etc. Also, the solid formulations may include, in addition to a simple excipient, a lubricant such as magnesium stearate or talc.

Examples of liquid formulations for oral administration include suspensions, internal solutions, emulsions and syrups. The liquid formulations may include, in addition to commonly used simple diluents such as water and liquid paraffin, various excipients, which are exemplified by humectants, sweeteners, aromatics and preservatives.

Examples of preparations for parenteral administration include sterile aqueous solutions, non-aqueous solutions, suspensions, emulsions, freeze-dried preparations and suppositories. In the formulation into non-aqueous solutions and suspensions, propylene glycol, PEG, vegetable oils such as olive oil, and injectable esters such as ethyl oleate may be used. Bases of injectable preparations may include conventional additives, such as solubilizers, isotonic agents, suspending agents, emulsifiers, stabilizers and antiseptics.

The term "administration", as used herein, means the introduction of a predetermined amount of a substance into a patient by a certain suitable method. The complex of the present invention may be administered via any of the common routes, as long as it is able to reach a desired tissue. Also, the present composition may be administered using a certain apparatus capable of transporting the active ingredient into a target cell.

In the present invention, a "patient" refers to a human or an animal such as a monkey, dog, goat, pig, rat or mouse, the human or animal having a disease whose symptoms are capable of being improved through the administration of the present composition. The composition according to the present invention may be applied to humans (for therapeutic, inhibitory or preventive purposes), as well as being applicable to other commercially useful animals.

In another aspect, the present invention provides a method of preventing and treating cancer by administering, to a patient, a composition comprising one or more selected from the group consisting of the compound of Chemical Formula 1 and pharmaceutically acceptable salts thereof. The present composition may be administered in combination with conventional therapeutic agents for a disease of interest.

The present composition may be administered in a pharmaceutically effective amount.

The term "pharmaceutically effective amount", as used herein, refers to an amount sufficient for the treatment or prevention of diseases, which is commensurate with a reasonable benefit/risk ratio applicable for medical treatment or prevention. An effective dosage of the present composition may be determined depending on the patient's diseases and severity of the diseases, drug activity, the patient's drug sensitivity, administration time, administration routes, excretion rates, duration of treatment, simultaneously used drugs, and other factors known in medicine. The present composition may be administered as a sole therapeutic agent or in combination with other therapeutic agents, and may be administered sequentially or simultaneously with conventional therapeutic agents. This administration may be provided in single or multiple doses. Taking all factors into consideration, it is important to conduct administration of minimal doses capable of giving the greatest effects with no adverse effects, such doses being readily determined by those skilled in the art.

In detail, the dosage of the present composition may vary depending on the patient's age, gender and weight, but the compound is typically administered in a dosage ranging from 5 to 50 mg, preferably 5 to 20 mg, per kg of weight every day or every two days. The dosage may be administered in a single daily dose or three divided daily doses. However, the dosage may be increased or decreased according to the administration route, severity of the illness, the patient's gender, weight and age, and the like. The above dosage does not limit the scope of the present invention, regardless of the dosage method.

A better understanding of the present invention may be obtained through the following examples which are set forth to illustrate, but are not to be construed as the limit of the present invention.

EXAMPLE 1

Inhibitory Activity Against STAT3

A dual luciferase assay was performed to determine whether the oxadiazole urea compound of the present invention has inhibitory activity against STAT3.

Colorectal carcinoma HCT116 cells were co-transfected with a plasmid carrying firefly luciferase, whose expression increases with STAT3 activity, and another plasmid carrying renilla luciferase, which is expressed independently of STAT3 activity. The transfected HCT116 cells were detached using 0.05% trypsin EDTA and seeded onto a 96-well test plate at a density of $1\times10^4$ cells per well. Cells were cultured in an incubator at 37☐ under 5% $CO_2$ for 3 hrs, and then incubated with DMSO (1%) alone as a control and with the oxadiazole urea compound (dissolved in DMSO) at various concentrations (diluted 1/100).

After 12 hrs or 24 hrs, STAT activity was assayed by adding two different substrates for firefly luciferase and renilla luciferase, beetle luciferin and coelenterazine, to the medium. The luminescence intensity by substrate degradation was measured using a luminometer (Wallac 1420). The measured firefly luciferase activity reflected STAT3 activity in a proportional manner. Renilla luciferase was used to calibrate non-specific cytotoxicity, occurring in each test group, and internal deviation.

The dual luciferase assay revealed that the oxadiazole urea compound inhibited 50% of STAT3 activity at 2.5 to 3.0 µM.

EXAMPLE 2

Inhibitory Activity Against the Growth of Cancer Cell Lines

The oxadiazole urea compound of the present invention was estimated for growth inhibitory activity against other human cancer cell lines in a WST-1 assay.

Human cancer cell lines were cultured in 10% fetal bovine serum (FBS)-containing medium at 37☐ under 5% $CO_2$, and detached using 0.05% trypsin-EDTA. Cells were seeded onto a 96-well plate at a density of $5\times10^3$ cells per well (for MDA-MB-231 and MDA-MB-468 breast cancer cells) or at a density of $7\times10^3$ cells per well (for colorectal carcinoma HCT116 and colon cancer SW620 cells).

Then, cells were cultured in 10% FBS containing medium in an incubator at 37☐ under 5% $CO_2$. After 24 hrs, the medium was exchanged with a medium containing 0.1% DMSO (as a control), or with media containing the oxadiazole urea compound at various concentrations (the compound dissolved in DMSO was diluted in medium), and cells were further cultured for 24 hrs. 10 µl of WST-1 Reagent (Roche) was added to each well, and the plate was incubated for 2 hrs. Absorbance was measured at 450 nm using an ELISA reader (Bio-Rad).

50% cell growth inhibition was observed in each cancer cell line at 15 to 80 µM of the present compound. The present compound exhibited the highest growth inhibitory activity against HCT116 cells with a $GI_{50}$ value of 15 µM. The present compound displayed $GI_{50}$ values of 40 µM and 70 µM toward MDA-MB-468 and SW620 cells, respectively, but did not show 50% growth inhibition toward MDA-MB-231 at concentrations less than 100 µm.

EXAMPLE 3

Acute Toxicity Test on Oral Application in Rats

An acute toxicity test was conducted with 6-week-old specific pathogen-free (SPF) SD rats. The present compound was suspended in injectable distilled water, and orally administered to two SD rats per group at a single dose of 1 g/kg/ml. After the present compound was administered, the rats were observed for mortality, clinical signs and body weight change, and hematological and hematobiochemical tests were performed. After autopsy, abnormalities of abdominal and thoracic organs were visually observed.

All rats administered with the compound exhibited no special clinical symptoms and no death. Also, no effects were observed on weight change and hematological, hematobiochemical and autopsy findings.

What is claimed is:

1. A method for inhibiting cancer cell growth in vitro comprising:
    administering an effective amount of a compound of Chemical Formula 1:

[Chemical Formula 1]

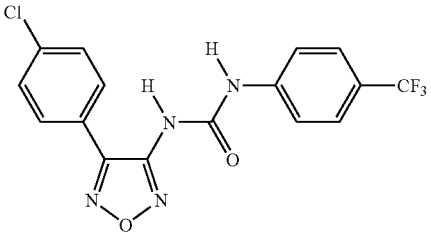

or a pharmaceutically acceptable salt thereof to a cancer cell, wherein the cancer is selected from the group consisting of colorectal cancer, prostate cancer, breast cancer, and colon cancer.

2. The method of claim 1, wherein the compound inhibits growth of cancer cells in vitro.

* * * * *